(12) United States Patent
Lee et al.

(10) Patent No.: US 10,307,490 B2
(45) Date of Patent: Jun. 4, 2019

(54) LIPID NANOPARTICLE COMPOSITIONS FOR ANTISENSE OLIGONUCLEOTIDES DELIVERY

(71) Applicant: The Ohio State University, Columbus, OH (US)

(72) Inventors: Robert J. Lee, Columbus, OH (US); Young Bok Lee, Clarksburg, MD (US); Deog Joong Kim, Rockville, MD (US); Chang Ho Ahn, Potomac, MD (US)

(73) Assignee: The Ohio State University, Columbus, OH (US)

( * ) Notice: Subject to any disclaimer, the term of this patent is extended or adjusted under 35 U.S.C. 154(b) by 0 days.

(21) Appl. No.: 13/900,969

(22) Filed: May 23, 2013

(65) Prior Publication Data

US 2013/0315937 A1 Nov. 28, 2013

Related U.S. Application Data

(60) Provisional application No. 61/784,892, filed on Mar. 14, 2013, provisional application No. 61/650,729, filed on May 23, 2012.

(51) Int. Cl.
| | | |
|---|---|---|
| *A61K 38/08* | (2006.01) | |
| *A61K 45/06* | (2006.01) | |
| *A61K 9/127* | (2006.01) | |
| *A61K 31/7088* | (2006.01) | |
| *C12N 15/113* | (2010.01) | |
| *A61K 31/713* | (2006.01) | |
| *A61K 47/64* | (2017.01) | |
| *A61K 38/10* | (2006.01) | |
| *A61K 38/48* | (2006.01) | |
| *C07K 16/00* | (2006.01) | |
| *A61K 47/54* | (2017.01) | |
| *A61K 47/59* | (2017.01) | |
| *A61K 47/69* | (2017.01) | |
| *A61K 48/00* | (2006.01) | |

(52) U.S. Cl.
CPC ............ *A61K 47/643* (2017.08); *A61K 9/127* (2013.01); *A61K 9/1271* (2013.01); *A61K 9/1272* (2013.01); *A61K 31/7088* (2013.01); *A61K 31/713* (2013.01); *A61K 38/08* (2013.01); *A61K 38/10* (2013.01); *A61K 38/482* (2013.01); *A61K 45/06* (2013.01); *A61K 47/543* (2017.08); *A61K 47/59* (2017.08); *A61K 47/6911* (2017.08); *C07K 16/00* (2013.01); *C12N 15/113* (2013.01); *C12N 15/1135* (2013.01); *C12N 15/1137* (2013.01); *A61K 48/00* (2013.01); *C12N 2310/11* (2013.01); *C12N 2310/14* (2013.01); *C12Y 304/21064* (2013.01)

(58) Field of Classification Search
None
See application file for complete search history.

(56) References Cited

U.S. PATENT DOCUMENTS

| | | | | |
|---|---|---|---|---|
| 5,908,777 | A * | 6/1999 | Lee ..................... | C12N 15/88 264/4.1 |
| 6,395,253 | B2 * | 5/2002 | Levy .................. | A61K 9/5153 424/1.25 |
| 6,821,955 | B2 | 11/2004 | Orson et al. | |
| 7,025,987 | B2 | 4/2006 | Cheresh et al. | |
| 7,060,291 | B1 | 6/2006 | Meers et al. | |
| 2001/0038851 | A1 * | 11/2001 | Allen et al. ................... | 424/450 |
| 2002/0022264 | A1 * | 2/2002 | Sullivan et al. ........... | 435/320.1 |
| 2003/0203865 | A1 * | 10/2003 | Harvie et al. .................. | 514/44 |
| 2004/0265999 | A1 * | 12/2004 | Yoon et al. .................... | 435/375 |
| 2010/0239654 | A1 | 9/2010 | Winter | |
| 2011/0117026 | A1 * | 5/2011 | Tseng .................. | A61K 9/1271 424/9.6 |

(Continued)

FOREIGN PATENT DOCUMENTS

| | | |
|---|---|---|
| CN | 1701077 A | 11/2005 |
| CN | 1809583 A | 7/2006 |

(Continued)

OTHER PUBLICATIONS

Thöle et al (Journal of Drug Targeting, 2002 vol. 10 (4), pp. 337-344).*
Attachment A, Theoretical pI for bovine serum albumin, Nov. 20, 2014.*
Attachment B, Theoretical pI for bovine serum albumin with 43 additional lysine residues, Nov. 20, 2014.*
Saul et al (Journal of Controlled Release 92 (2003) 49-67).*
Translation of CN 102552105 retrieved from http://www.google.com/patents/CN102552105A?cl=en on Apr. 6, 2015.*
Fischer et al (International Journal of Pharmaceutics 225 (2001) 97-111).*

(Continued)

*Primary Examiner* — Richard A Schnizer
(74) *Attorney, Agent, or Firm* — Meunier Carlin & Curfman LLC

(57) ABSTRACT

Described is a lipid nanoparticle composition that includes a macromolecule conjugated to a polymer and a targeting agent. The composition can include a therapeutic agent. The therapeutic agent can be an antisense oligonucleotide (ASO). Exemplary ASOs are targeted to a portion of a nucleic acid encoding Akt-1, and which modulates the expression of Akt-1; or targeted to a portion of a nucleic acid encoding HIF-1, and which modulates the expression of HIF-1. Also described is a lipid nanoparticle composition that includes a macromolecule conjugated to a polymer and a therapeutic agent that is an ASO such as an ASO targeted to a portion of a nucleic acid encoding Akt-1, and which modulates the expression of Akt-1 or an ASO targeted to a portion of a nucleic acid encoding HIF-1, and which modulates the expression of HIF-1. Pharmaceutical formulations, methods of making the lipid nanoparticles, and methods of using the lipid nanoparticles, for example for treating cancers, are also disclosed.

32 Claims, 7 Drawing Sheets

Specification includes a Sequence Listing.

(56) References Cited

U.S. PATENT DOCUMENTS

| | | | |
|---|---|---|---|
| 2011/0160283 A1* | 6/2011 | Bennett | C12N 15/1138 514/44 A |
| 2011/0177155 A1 | 7/2011 | Peer et al. | |
| 2011/0243880 A1* | 10/2011 | Yurkovetskiy et al. | 424/78.17 |
| 2011/0256059 A1* | 10/2011 | Sanchez Barreiro et al. | 424/9.1 |
| 2012/0058144 A1 | 3/2012 | Manoharan et al. | |

FOREIGN PATENT DOCUMENTS

| | | | |
|---|---|---|---|
| CN | 102552105 | * | 7/2012 |
| JP | 2003-501460 A | | 1/2003 |
| JP | 2006-504410 A | | 2/2006 |
| JP | 2006-111591 A | | 4/2006 |
| JP | 2015-523969 A | | 8/2015 |
| JP | 2015-525209 A | | 9/2015 |
| WO | WO-9700965 A2 | | 1/1997 |
| WO | WO-2004066949 A2 | | 8/2004 |
| WO | WO-2009120247 A2 | | 10/2009 |

OTHER PUBLICATIONS

Orson et al (J Immunol 2000; 164:6313-6321).*
Han et al (small 10(3)524-535, 2014).*
Munoz-Ubeda et al (Soft Matter, 2011, 7, 5991).*
Eisele et al (Biomaterials 31 (2010) 8789e8801).*
Eisele et al (Biomaterials 31 (2010) 8789e8801 supporting Information).*
Li (Mol. Pharmacol. 3(5): 579-588, 2006) (Year: 2006).*
Wei Wang et al. "Transferrin-PEG-PE modified dexamethasone conjugated cationic lipid carrier mediated gene delivery system for tumor-targeted transfection," International Journal of Nanomedicine, May 1, 2012, p. 2513.
International Search Report issued in PCT/US2013/042454 with Written Opinion, dated Aug. 2, 2013.
Weecharangsan et al., Efficient Delivery of Antisense Oligodeoxyribonucleotide G3139 by Human Serum Albumin-Coated Liposomes, Mol Pharm, pp. 1-18, Dec. 7, 2010, vol. 6, No. 6.
Yuan et al., High PEGylation Efficiency of Pentaethylenehexamine-End Poly (Ethylene Glycol) (mPEG-N6) for Active-Ester Surface, Colloids and Surfaces B: Biointerfaces, Nov. 11, 2011, vol. 92, pp. 25-29.
Huang et al., Non-viral Vectors for gene Therapy, Part 1, Advances in Genetics, 2005, vol. 53.
Petersen, H., Structurally Modifies Polyethylenimines and Their Interpolyelectrolyte Complexes with DNA as Non-Viral Gene Delivery Systems, Dissertation, Phillipps-Universitat Marbug, Jul. 3, 202, pp. 75.
International Search Report in Patent Application No. PCT/US13/42461, dated Dec. 17, 2013.
Weecharangsan et al, "Disulfide-linked Liposomes: Effective Delivery Vehicle for Bcl-2 Antisense Oligodeoxyribonucleotide G3139," Aniticancer Research 30: 31-38 (2010).
Smolarczyk et al., "Negligible induction of IFN-gamma, IL-12 and TNF-alpha by DNA-PEI 750 kDa/albumin complexes," Cytokine, Academic Press Ltd., Philadelphia, PA US, vol. 29, No. 6, Mar. 21, 2005, pp. 283-287.
Piao et al., "Human serum albumin-coated lipid nanoparticles for delivery of si RNA to breast cancer", Nanomedicine: Nanotechnology, Biology and Medicine, vol. 9, Issue 1, Jan. 2013, pp. 122-129.
Rhaese et al., "Human serum albumin-polyethylenimine nanoparticles for gen delivery", Journal of Controlled Release, vol. 92, (2003), pp. 199-208.
Charnonneau et al., "Structural Analysis of Human Serum Albumin Complexes with Cationic Lipids", J. Phys. Chem. B 2009, vol. 113, pp. 1777-1784.
Maurer et al., "Spontaneous Entrapment of Polynucleotides upon Electrostatic Interaction with Ethanol-Destabilized Cationic Liposomes", Biophysical Journal, vol. 80, May 2001, pp. 2310-2326.

* cited by examiner

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gctgcatgat ctccttggcg                                                   20

<210> SEQ ID NO 2
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 2
aatgagccac cagtgtccaa                                                20

<210> SEQ ID NO 3
<211> LENGTH: 20
<212> TYPE: DNA
<213> ORGANISM: Homo sapiens

<400> SEQUENCE: 3
cgccaaggag atcatgcagc                                                20

<210> SEQ ID NO 4
<211> LENGTH: 20
<212> TYPE: DNA
<213> ORGANISM: Homo sapiens

<400> SEQUENCE: 4
agtggactgg tggggctgg                                                 20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
agatagctgg tgacagacag                                                20

<210> SEQ ID NO 6
<211> LENGTH: 20
<212> TYPE: DNA
<213> ORGANISM: Homo sapiens

<400> SEQUENCE: 6
ctgtctgtca ccagctatct                                                20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cgtggagaga tcatctgagg                                                20

<210> SEQ ID NO 8
<211> LENGTH: 20
<212> TYPE: DNA
<213> ORGANISM: Homo sapiens

<400> SEQUENCE: 8
cctcagatga tctctccacg                                                20

<210> SEQ ID NO 9
<211> LENGTH: 20
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 9
tcgaaaaggt caagtgctac                                                      20

<210> SEQ ID NO 10
<211> LENGTH: 20
<212> TYPE: DNA
<213> ORGANISM: Homo sapiens

<400> SEQUENCE: 10
gtagcacttg accttttcga                                                      20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tggtgcagcg gcagcggcag                                                      20

<210> SEQ ID NO 12
<211> LENGTH: 20
<212> TYPE: DNA
<213> ORGANISM: Homo sapiens

<400> SEQUENCE: 12
ctgccgctgc cgctgcacca                                                      20

<210> SEQ ID NO 13
<211> LENGTH: 20
<212> TYPE: DNA
<213> ORGANISM: Homo sapiens

<400> SEQUENCE: 13
gctaggcccg cgctcgcgcc                                                      20

<210> SEQ ID NO 14
<211> LENGTH: 20
<212> TYPE: DNA
<213> ORGANISM: Homo sapiens

<400> SEQUENCE: 14
ttggacactg gtggctcatt                                                      20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ggagctaaca tctccaagtc                                                      20

<210> SEQ ID NO 16
<211> LENGTH: 20
<212> TYPE: DNA
<213> ORGANISM: Homo sapiens

```
<400> SEQUENCE: 16
gacttggaga tgttagctcc                                                                        20
```

LIPID NANOPARTICLE COMPOSITIONS FOR ANTISENSE OLIGONUCLEOTIDES DELIVERY

RELATED APPLICATIONS

This application claims priority to U.S. Provisional Application No. 61/650,729, filed May 23, 2012 and U.S. Provisional Application No. 61/784,892, filed Mar. 14, 2013, the contents of which are hereby incorporated by reference in the entirety.

STATEMENT REGARDING FEDERALLY SPONSORED RESEARCH

This invention was made with government support under Grant Numbers R01 CA135243, DK088076, and CA152969 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on May 23, 2013, is named 41890-349708_SL.txt and is 3,304 bytes in size.

TECHNICAL FIELD

The present disclosure describes lipid nanoparticles usable for the delivery of nucleic acids and related compounds.

BACKGROUND OF THE INVENTION

Delivery of siRNA and other therapeutic oligonucleotides is a major technical challenge that has limited their potential for clinical translation.

A liposome is a vesicle composed of one or more lipid bilayers, capable of carrying hydrophilic molecules within an aqueous core or hydrophobic molecules within its lipid bilayer(s). Lipid nanoparticles (LNs) is a general term to described lipid-based particles in the submicron range. They can have structural characteristics of liposomes and/or have alternative non-bilayer types of structures. Drug delivery by LNs via systemic route requires overcoming several physiological barriers. The reticuloendothelial system (RES) can be responsible for clearance of LNs from the circulation. Once escaping the vasculature and reaching the target cell, LNs are typically taken up by endocytosis and must release the drug into the cytoplasm prior to degradation within acidic endosome conditions.

Consideration of zeta potential or surface charge is necessary when preparing LNs. The zeta potential of LNs typically should not be excessively positive or too negative for systemic delivery. LNs with a highly positive charge tend to interact non-specifically with target cells and circulating plasma proteins, and may cause cytotoxicity. Alternatively, LNs with a highly negative charge cannot effectively incorporate nucleic acids, which are also negatively charged, and may trigger rapid RES-mediated clearance, reducing therapeutic efficacy. LNs with a neutral to moderate charge are best suited for in vivo drug and gene delivery.

LNs constitute a promising platform for the delivery of traditional therapeutic compounds and nucleic acid-based therapies. Drugs formulated using LNs can often feature superior pharmacokinetic (PK) properties in vivo, such as increased blood circulation time and increased accumulation at the site of solid tumors due to enhanced permeability and retention (EPR) effect. Moreover, LNs may be surface-coated with polyethylene glycol to reduce opsonization of LNs by serum proteins and the resulting RES-mediated uptake. LNs can also be coated with cell-specific ligands to provide targeted drug delivery.

Much interest has arisen over nucleic acid-based therapies over the past few decades. Nucleic acid-based therapies work on the premise of introducing nucleic acids (NAs) to promote or inhibit gene expression. As mutations in genes and changes in miRNA profile are believed to be the underlying cause of cancer and other diseases, nucleic acid-based agents potentially can directly act upon the underlying etiology, maximizing therapeutic potential. A few examples of nucleic acid-based therapies include plasmid DNA (pDNA), small interfering RNA (siRNA), small hairpin RNA (shRNA), microRNA (miR) mimic (or mimetic), anti-miR/antagomiR/miR inhibitor, and antisense oligonucleotide (ASO), each of which is encompassed by the term nucleic acid as used in the present disclosure. The clinical translation of nucleic acid-based therapies faces several obstacles in its implementation. Transporting nucleic acids to their intracellular target is particularly challenging as nucleic acids are relatively unstable and are subject to degradation by serum and cellular nucleases. Further, the high negative charges of nucleic acids make it impossible for transport across the cell membrane, limiting utility. Viral vectors have been developed to address this issue, but most have failed due to activation of immunological responses in vivo and induction of undesired mutations in the host genome. Non-viral vectors have also been investigated extensively, but few have yielded successful clinical outcomes and further improvements are needed.

Traditionally, cationic LNs have been utilized as non-viral vectors for gene delivery. In some instances, cationic lipids are replaced with, or used in combination with, anionic lipids. The positive charge of cationic LNs facilitates an electrostatic interaction with negatively charged nucleic acids. Anionic lipids can be combined with cationic lipids or with a cationic polymer, which will in turn mediate interaction with the nucleic acids. These may be prepared by various techniques known in the art such as ethanol dilution, freeze-thaw, diafiltration, and thin film hydration. In addition to cationic components, LNs are typically composed of helper lipids, including bilayer-forming phospholipid components such as phosphatidylcholines, as well as cholesterol. Helper lipids such as dioleoylphosphatidylethanolamines (DOPE) do not favor bilayer phase and instead aid in disrupting the lipid bilayer at the target site to release the therapeutic agent. Stabilizing components such as D-alpha tocopheryl polyethylene glycol 1000 succinate (TPGS), which is a PEGylating agent, or mPEG-DSPE may be added to stabilize the formulation and protect the LN from RES-mediated uptake.

The development of efficient delivery vehicles is a key to clinical translation of oligonucleotide (ON) therapeutics. Ideally, a lipid nanoparticle formulation should be able to (1) protect the drug from enzymatic degradation; (2) traverse the capillary endothelium; (3) specifically reach the target cell type without causing immunogenicity or off-target cytotoxicity; (4) promote endocytosis and endosomal release; and (5) form a stable formulation with colloidal stability and long shelf-life.

SUMMARY OF THE INVENTION

Provided herein are lipid nanoparticles that can encapsulate therapeutic oligonucleotides with high efficiency and fulfill physical and biological criteria for efficacious delivery. In the present invention, certain embodiments includes lipid nanoparticles containing RX-0201 (Archexin®), which is a 20-mer phosphorothioate antisense oligonucleotide having a sequence that includes 5' gctgcatgatctccttggcg 3' (Seq. Id. No.: 1) against Akt-1, and/or RX-0047, which is a 20-mer phosphorothioate antisense oligonucleotide having a sequence that includes 5' aatgagccaccagtgtccaa 3' (Seq. Id. No.: 2), that is a potent inhibitor of "Hypoxia inducible factor-1 alpha" (HIF-1α).

In certain embodiments, the lipid nanoparticles comprise hyper-cationized and/or pH-responsive HSA-polymer conjugates. In certain embodiments, the HSA-polymer conjugate comprises HSA-PEHA. In certain embodiments, the lipid nanoparticles hyper-cationized albumin-polymer conjugates (APC) in order to increase the transfection efficiency of lipid nanoparticle formulations.

Further provided herein are pharmaceutical compositions, methods of making a lipid-coated albumin nanoparticles, and methods of treating a cancer or other disease.

In embodiments, the present invention is a lipid nanoparticle composition that includes a macromolecule conjugated to a polymer and a targeting agent. In embodiments, the lipid nanoparticle composition also includes a therapeutic agent such as nucleic acids, proteins, polysaccharides, lipids, radioactive substances, therapeutic agents, prodrugs, and combinations thereof. In embodiments, the therapeutic agent is a nucleic acid. In some embodiments, the nucleic acid is pDNAs, antisense oligonucleotides, miR5, antimiR5, shRNAs, siRNAs, or combinations thereof. In embodiments, the therapeutic agent is an antisense oligonucleotide (ASO) that can be an ASO targeted to a portion of a nucleic acid encoding Akt-1, and which modulates the expression of Akt-1; or an ASO targeted to a portion of a nucleic acid encoding HIF-1, and which modulates the expression of HIF-1.

Embodiments of the present invention also include a lipid nanoparticle composition that includes a macromolecule conjugated to a polymer and a therapeutic agent that is an ASO such as an ASO targeted to a portion of a nucleic acid encoding Akt-1, and which modulates the expression of Akt-1 or an ASO targeted to a portion of a nucleic acid encoding HIF-1, and which modulates the expression of HIF-1.

In any of the embodiment of the invention, the polymer can be charged, for example the polymer can be positively charged. In embodiments of the invention, the macromolecule includes albumin. In exemplary embodiments the macromolecule conjugated to a polymer is an albumin-polycation conjugate. Conjugation can be, for example, via cross linking agents. The macromolecule or positively charged polymer can be, for example, pentaethylenehexamine (PEHA), tetraethylenehexamine, and tetraethylenepentamine (TEPA). In embodiments, the macromolecule includes pentaethylenehexamine (PEHA) and the polymer includes human serum albumin (HSA). The ratio of PEHA molecules to HSA molecules can be about 11 to 1. The lipid nanoparticle of the invention can include a mixture of two or more low molecular weight polymers. The lipid nanoparticle can include DOTAP, SPC, and TPGS, for example a molar ratio of DOTAP:SPC:TPGS at about 25:70:5.

In embodiments that include an ASO, the antisense oligonucleotide is a compound having a sequence that includes 5' gctgcatgatctccttggcg 3'(Seq. Id. No.: 1), targeted to a nucleic acid molecule encoding human Akt-1, and which modulates the expression of Akt-1. In other embodiments, the antisense oligonucleotide is a compound having a sequence that includes 5' aatgagccaccagtgtccaa 3'(Seq. Id. No.: 2), targeted to a nucleic acid molecule encoding human HIF-1, and which modulates the expression of HIF-1. The lipid nanoparticle composition can also include a fusogenic peptide. In embodiments, the lipid nanoparticle has a particle size under about 300 nm or under about 150 nm.

The targeting agent can be bound only to an external surface of the lipid nanoparticle via direct connection or via a crosslinker. The targeting agent can be an antibody or an antibody fragment. The targeting agent can also be a cRGD peptides, galactose-containing moieties, transferrin, folate, low density lipoprotein, and epidermal growth factors. In exemplary embodiments, the targeting agent is cRGDfC, or folate. The targeting agent can be a conjugate such as folate-PEG-CHEMS (folate-polyethylene glycol-cholesteryl hemisuccinate), folate-PEG-DSPE (folate-polyethylene glycol-distearoyl phosphatidylethanolamine), or cRGDfC-PEG-DSPE (cyclo(RGDfC)-polyethylene glycol-distearoyl phosphatidylethanolamine).

In embodiments, the invention is a pharmaceutical composition comprising a lipid nanoparticle composition as described above and a pharmaceutically acceptable excipient. The pharmaceutical composition can be prepared as a sterile solution or suspension.

In other embodiments, the invention is a method of making a lipid-coated albumin nanoparticle (LCAN), wherein the method includes the steps of synthesizing a HSA-PEHA conjugate; preparing a mixture of lipids; adding the mixture of lipids to the HSA-PEHA conjugate; and adding an antisense oligonucleotide (ASO) to the mixture of lipids and the HSA-PEHA conjugate to obtain an LCAN precursor; wherein the ASO is selected from the group consisting of an ASO targeted to a portion of a nucleic acid encoding Akt-1, and which modulates the expression of Akt-1; and an ASO targeted to a portion of a nucleic acid encoding HIF-1, and which modulates the expression of HIF-1. In other embodiments, the invention is a method of making a lipid-coated albumin nanoparticle (LCAN), that includes the steps of synthesizing a HSA-PEHA conjugate; preparing a mixture of lipids; and adding a targeting agent and the mixture of lipids to the HSA-PEHA conjugate. The targeting agent can be any of the targeting agents as described above. In embodiments, mixture of lipids comprises and targeting agent includes DOTAP, soyPC, TPGS, and cRGDfC-PEG-DSPE, for example wherein the molar ratio of DOTAP:soyPC:TPGS:cRGD-PEG-DSPE is about 25:70:4:1. In other embodiments, the mixture of lipids includes DOTAP, SPC, and TPGS, for example in a molar ratio of about 25:70:5.

The invention is also a method of diagnosing or treating a cancer or infectious disease, by administering an effective amount of a pharmaceutical composition as described herein to a patient in need thereof. The cancer treated can be, for example, brain cancer, bladder cancer, lung cancer, breast cancer, melanoma, skin cancer, epidermal carcinoma, colon and rectal cancer, non-Hodgkin lymphoma, endometrial cancer, pancreatic cancer, kidney (renal cell) cancer, prostate cancer, leukemia thyroid cancer, head and neck, ovarian cancer, hepatocellular cancer, cervical cancer, sarcomas, gastric cancers, multiple myeloma, lymphomas, and gastrointestinal cancer, and uterine cancer. In some embodiments, the cancer is breast cancer, epidermal carcinoma, or pancreatic cancer.

Further objectives and advantages, as well as the structure and function of preferred embodiments will become apparent from a consideration of the description, drawings, and non-limiting examples that follow.

DETAILED DESCRIPTION OF THE INVENTION

Figure 1:
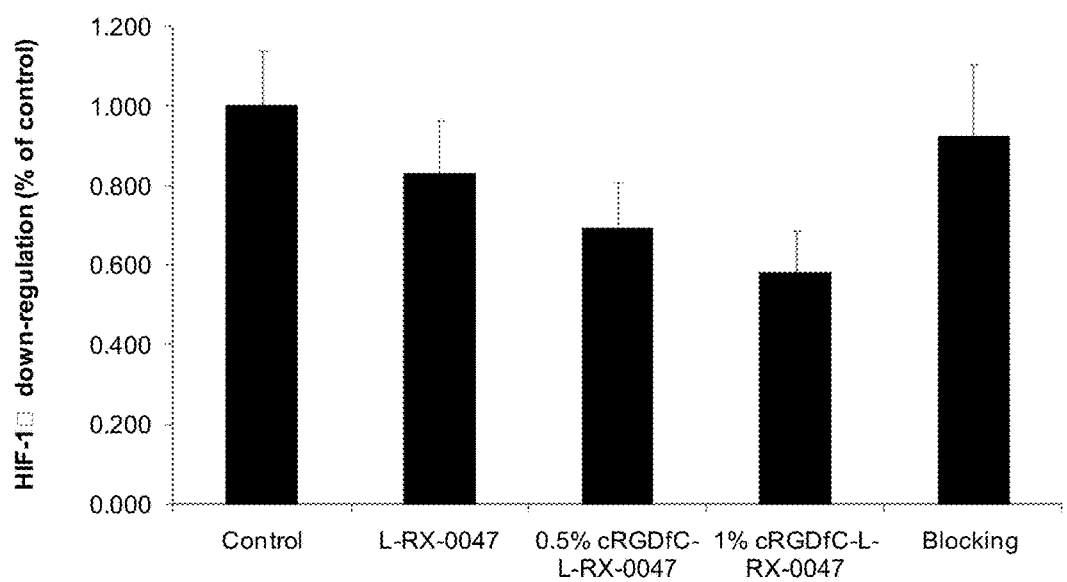
FIG. 1 illustrates HIF-1α mRNA down-regulation in MDA-MB-435 cells upon treatment with L-RX-0047 and cRGD-L-RX-0047.

Various embodiments are described herein in the context of lipid nanoparticles. Those of ordinary skill in the art will realize that the following detailed description of the embodiments is illustrative only and not intended to be in any way limiting. Other embodiments will readily suggest themselves to such skilled persons having the benefit of this disclosure. Reference to an "embodiment," "aspect," or "example" herein indicate that the embodiments of the invention so described may include a particular feature, structure, or characteristic, but not every embodiment necessarily includes the particular feature, structure, or characteristic. Further, repeated use of the phrase "in one embodiment" does not necessarily refer to the same embodiment, although it may.

In the interest of clarity, not all of the routine features of the implementations or processes described herein are shown and described. It will, of course, be appreciated that in the development of any such actual implementation, numerous implementation-specific decisions will be made in order to achieve specific goals, such as compliance with application, therapy and subject related constraints, and that these specific goals will vary from one implementation to another and from one user to another. Moreover, it will be appreciated that such development efforts might be complex and time-consuming, but would nevertheless be a routine undertaking for those of ordinary skill in the art having the benefit of this disclosure.

Provided herein are lipid nanoparticles (LNs) with improved transfection activity. The lipid nanoparticles may partition hydrophobic molecules within the lipid membrane and/or encapsulate water-soluble particles within the aqueous core. The LN formulations can comprise a single lipid or a mixture of lipids, generally including a charged lipid and a neutral lipid, and optionally further including a PEGylating lipid and/or cholesterol. The LN formulations of the present disclosure may include albumin-polymer conjugates. In certain embodiments, the lipid nanoparticles comprise hyper-cationized albumin-polycation conjugates (APCs). The LNs can have a diameter of less than 300 nm, or typically between about 50 nm and about 200 nm. LNs according to the invention can exhibit one or more advantages such as enhanced transfection and reduced cytotoxicity, especially under high serum conditions found during systemic administration. The LNs are applicable to a wide range of current therapeutic agents and systems, and can exhibit serum stability, targeted delivery, and/or high transfection efficiency.

The term "lipid nanoparticle" as used herein refers to any vesicles formed by one or more lipid components. The LN formulations described herein may include cationic lipids. Cationic lipids are lipids that carry a net positive charge at any physiological pH. The positive charge is used for association with negatively charged therapeutics such as ASOs via electrostatic interaction. Suitable cationic lipids include, but are not limited to: 3β-[N—(N',N'-dimethylaminoethane)-carbamoyl]cholesterol hydrochloride (DC-Chol); 1,2-dioleoyl-3-trimethylammonium-propane (DOTAP); 1,2-dioleoyl-3-dimethylammonium-propane (DODAP); dimethyldioctadecylammonium bromide salt (DDAB); 1,2-dilauroyl-sn-glycero-3-ethylphosphocholine chloride (DL-EPC); N-[1-(2,3-dioleyloyx) propyl]-N—N—N-trimethyl ammonium chloride (DOTMA); N-[1-(2,3-dioleyloyx) propyl]-N—N—N-dimethyl ammonium chloride (DODMA); 1,2-dilauroyl-sn-glycero-3-ethylphosphocholine chloride (DOEPC); N,N-dioctadecyl-N,N-dimethylammonium chloride (DODAC); N-(1-(2,3-dioleyloxy)propyl)-N-2-(sperminecarboxamido)ethyl)-N,N-dimethylammonium trifluoracetate (DOSPA); 1,2-dimyristyloxypropyl-3-dimethylhydroxyethyl ammonium bromide (DMRIE); dioctadecylamidoglycylspermine (DOGS); neutral lipids conjugated to cationic modifying groups; and combinations thereof. In addition, a number of cationic lipids in commercially available preparations could be used, such as LIPOFECTIN (from GIBCO/BRL), LIPOFECTAMINE (from GIBCO/MRL), siPORT NEOFX (from Applied Biosystems), TRANSFECTAM (from Promega), and TRANSFECTIN (from Bio-Rad Laboratories, Inc.). Other cationic lipids known in the art or developed subsequently may also be used in the invention. The skilled practitioner will recognize that many more cationic lipids are suitable for inclusion in the inventive LN formulations. The cationic lipids of the present disclosure may be present at concentrations ranging from about 0 to about 60.0 molar percent of the lipids in the formulation, or from about 5.0 to about 50.0 molar percent of the lipids in the formulation. As used herein, "formulation" refers to the lipid-coated albumin nanoparticle (LCAN) that includes the lipid nanoparticle and the cationized albumin-polymer conjugates identified herein that contain nucleic acids. The formulation also includes the targeting agent, when present.

The LN formulations presently disclosed may include anionic lipids. Anionic lipids are lipids that carry a net negative charge at physiological pH. These lipids, when combined with cationic lipids, are used to reduce the overall surface charge of LNs and introduce pH-dependent disruption of the LN bilayer structure, facilitating nucleotide release by inducing nonlamellar phases at acidic pH or induce fusion with the cellular membrane. Examples of suitable anionic lipids include, but are not limited to: fatty acids such as oleic, linoleic, and linolenic acids; cholesteryl hemisuccinate (CHEMS); 1,2-di-O-tetradecyl-sn-glycero-3- phospho-(1'-rac-glycerol) (Diether PG); 1,2-dimyristoyl-sn-glycero-3-phospho-(1'-rac-glycerol) (sodium salt); 1,2-dimyristoyl-sn-glycero-3-phospho-L-serine (sodium salt); 1-hexadecanoyl,2-(9Z,12Z)-octadecadienoyl-sn-glycero-3-phosphate; 1,2-dioleoyl-sn-glycero-3-[phospho-rac-(1-glycerol)] (DOPG); dioleoylphosphatidic acid (DOPA); and 1,2-dioleoyl-sn-glycero-3-phospho-L-serine (DOPS); anionic modifying groups conjugated to neutral lipids; and combinations thereof. Other anionic lipids known in the art or developed subsequently may also be used in the invention. The anionic lipids of the present disclosure are present at concentrations ranging from about 0 to about 60.0 molar percent of the formulation, or from about 5.0 to about 25.0 molar percent of the formulation.

Charged LNs are advantageous for transfection, but off-target effects such as cytotoxicity and RES-mediated uptake may occur. To attenuate cytotoxicity and/or RES-mediated uptake, hydrophilic molecules such as polyethylene glycol (PEG) may be conjugated to a lipid anchor and included in the LNs described herein to discourage LN aggregation or interaction with membranes. Hydrophilic polymers may be covalently bonded to lipid components or conjugated using crosslinking agents to functional groups such as amines. Suitable hydrophilic polymers for conjugation and hydrophilic polymer conjugates include, but are not limited to: polyvinyl alcohol (PVA); polysorbate 80; 1,2-distearoyl-sn-glycero-3-phosphoethanolamine-N-PEG2000 (DSPE-PEG2000); D-alpha-tocopheryl polyethylene glycol 1000 succinate (TPGS); dimyristoylphosphatidylethanolamine-PEG2000 (DMPE-PEG2000); and dipalmitoylphosphatidylethanolamine-PEG2000 (DPPE-PEG2000). Other hydrophilic polymers and conjugates known in the art or developed subsequently may also be used in the invention. The hydrophilic polymer may be present at concentrations ranging from about 0 to about 15.0 molar percent of the formulation, or from about 5.0 to about 10.0 molar percent of the formulation. The molecular weight of the hydrophilic polymer used, such as PEG, can be from about 100 and about 10,000 Da, from about 100 and about 5,000 Da or from about 100 to about 2,000 Da.

The LNs described herein may further comprise neutral and/or amphipathic lipids as helper lipids. These lipids are used to stabilize the formulation, reduce elimination in vivo, or increase transfection efficiency. The LNs may be formulated in a solution of saccharides such as, but not limited to, glucose, sorbitol, sucrose, maltose, trehalose, lactose, cellubiose, raffinose, maltotriose, dextran, or combinations thereof, to promote lyostability and cryostability.

Neutral lipids have zero net charge at physiological pH. One or a combination of several neutral lipids may be included in any LN formulation disclosed herein. Suitable neutral lipids include, but are not limited to: phosphatidylcholine (PC), phosphatidylethanolamine, ceramide, cerebrosides, prostaglandins, sphingomyelin, cephalin, cholesterol, diacylglycerols, glycosylated diacylglycerols, prenols, lysosomal PLA2 substrates, N-acylglycines, and combinations thereof.

Other suitable lipids include, but are not limited to: phosphatidylcholine, phosphatidic acid, phosphatidylethanolamine, phosphatidylglycerol, phosphatidylcholine, and lysophosphatidylethanolamine; sterols such as cholesterol, demosterol, sitosterol, zymosterol, diosgenin, lanostenol, stigmasterol, lathosterol, and dehydroepiandrosterone; and sphingolipids such as sphingosines, ceramides, sphingomyelin, gangliosides, glycosphingolipids, phosphosphingolipids, phytoshingosine; and combinations thereof.

The LN formulations described herein may further comprise fusogenic lipids or fusogenic coatings to promote membrane fusion. Examples of suitable fusogenic lipids include, but are not limited to, glyceryl mono-oleate, oleic acid, palmitoleic acid, phosphatidic acid, phosphoinositol 4,5-bisphosphate (PIP2), and combinations thereof. Other fusogenic lipids known in the art or developed subsequently may also be used in the invention.

The LN formulations described here may further comprise cationic polymers or conjugates of cationic polymers. Cationic polymers or conjugates thereof may be used alone or in combination with lipid nanocarriers. Suitable cationic polymers include, but are not limited to: polyethylenimine (PEI); pentaethylenehexamine (PEHA); spermine; spermidine; poly(L-lysine); poly(amido amine) (PAMAM) dendrimers; polypropyleneiminie dendrimers; poly(2-dimethylamino ethyl)-methacrylate (pDMAEMA); chitosan; tris(2-aminoethyl)amine and its methylated derivatives; and combinations thereof. Other Cationic polymers or conjugates known in the art or developed subsequently may also be used in the invention. Chain length and branching are considerations for the implementation of polymeric delivery systems. High molecular weight polymers such as PEI having a molecular weight of about 25,000 are used as transfection agents, but suffer from cytotoxicity. Low molecular weight polymers such as PEI having a molecular weight of about 600, may not cause cytotoxicity, but can be of limited use due to an inability to facilitate stable condensation with nucleic acids. Conjugation of low molecular weight polymers to larger particles such as albumin is a thus a useful method of increasing activity of nucleic acid condensation while lowering cytotoxicity in formulations.

Anionic polymers may be incorporated into the LN formulations presently disclosed as well. Suitable anionic polymers include, but are not limited to: poly(propylacrylic acid) (PPAA); poly(glutamic acid) (PGA); alginates; dextrans; xanthans; derivatized polymers; and combinations thereof. Other anionic polymers known in the art or developed subsequently may also be used in the invention.

In certain embodiments, the LN formulation includes conjugates of polymers. The conjugates may be crosslinked to targeting agents, lipophilic moieties, peptides, proteins, or other molecules that increase the overall therapeutic efficacy. Suitable crosslinking agents include, but are not limited to: N-succinimidyl 3-[2-pyridyldithio]-propionate (SPDP); dimethyl 3,3'-dithiobispropionimidate (DTBP); dicyclohexylcarbodiimide (DCC); diisopropyl carbodiimide (DIC); 1-ethyl-3-[3-dimethylaminopropyl]carbodiimide (EDC); N-hydroxysulfosuccinimide (Sulfo-NHS); N'—N'-carbonyldiimidazole (CDI); N-ethyl-5-phenylisoxazolium-3' sulfonate (Woodward's reagent K); and combinations thereof.

Various methods of LN preparation are suitable to synthesize the LNs of the present disclosure, including methods known in the art. For example, ethanol dilution, freeze-thaw, thin film hydration, sonication, extrusion, high pressure homogenization, detergent dialysis, microfluidization, tangential flow diafiltration, sterile filtration, and/or lyophilization may be utilized. Additionally, several methods may be employed to decrease the size of the LNs. For example, homogenization may be conducted on any devices suitable for lipid homogenization such as an Avestin Emulsiflex C5. Homogenized LNs may be recycled back into circulation for extended homogenization. Extrusion may be conducted on a Lipex Biomembrane extruder using a polycarbonate membrane of appropriate pore size (0.05 to 0.2 µm). Multiple particle size reduction cycles may be conducted to minimize size variation within the sample and achieve a desired size.

The resultant LNs may then be passed through a Sepharose CL4B to remove excess reagents or processed by tangential flow diafiltration.

Any embodiment of the LNs described herein may further include ethanol in the LN suspension. The incorporation of about 10-40% ethanol in LN formulations permeabilizes the lipid bilayer. Disruption of the lipid bilayer aids in condensation with charged moieties such as ASO and siRNA. LNs prepared in this manner are diluted before administration to reduce the effects of cellular membrane lysis due to the presence of ethanol. Alternatively, ethanol may be removed by dialysis and diafiltration, which also removes non-encapsulated nucleic acid.

The LNs can be sterilized. This may be achieved, for example, by passing of the LNs through a 0.2 or 0.22 µm sterile filter with or without pre-filtration.

Physical characterization of the LNs can be carried through many methods. Dynamic light scattering (DLS) or atomic force microscopy (AFM) can be used to determine the average diameter and its standard deviation. Ideally, LNs should fall under 200 nm in diameter. Zeta potential measurement via zeta potentiometer is useful in determining the relative stability of particles. Both dynamic light scattering analysis and zeta potential analysis may be conducted with diluted samples in deionized water or appropriate buffer solution. Cryogenic transmission electron microscopy (Cryo-TEM) and scanning electron microscopy (SEM) may be used to determine the detailed morphology of LNs.

The LNs described herein are stable under refrigeration for several months. LNs requiring extended periods of time between synthesis and administration may be lyophilized using standard procedures. A cryoprotectant such as 10% sucrose may be added to the LN suspension prior to freezing to maintain the integrity of the formulation. Freeze drying loaded LN formulations is recommended for long term stability.

APC

In addition to cationic lipids, cationic polymers are useful to nucleic acid delivery systems. The utilization of cationic polymers as transfection agents alone and in conjunction with LNs often benefits transfection efficiency. The most well-characterized polymeric transfection agent is high molecular weight polyethylenimine, a large polymer with a molecular weight of about 25 kDa, referred to herein as PEI25K. PEI25K has had great success in delivering pDNA to cells; however, cytotoxicity has limited its use. Less toxic, low molecular weight PEI having a molecular weight of about 600 kDa has also been investigated, but this has shown diminished ability to condense and deliver nucleic acids. In accordance with this, provided herein are hyper-cationized albumin-polymer conjugates (APCs). APCs may either be used alone to deliver agents such as pDNA or combined with lipid-based formulations to deliver agents such as siRNA or ASOs. Albumin also possesses endosomal lytic activity due to its hydrophobic core, which upon conformational change can be exposed and can induce bilayer disruption or membrane fusion. Albumin-PEI600 conjugates have an ionization profile that is responsive to pH change. The charge density is increased at endosomal pH.

In one embodiment, an APC is combined with a cationic lipid combination to assemble a cationic lipid-APC-nucleic acid nanoparticle. In another embodiment, an APC is combined with an anionic lipid combination to assemble a lipid-APC-nucleic acid nanoparticle. In certain embodiments, the lipid nanoparticles comprise hyper-cationized albumin-polycation conjugates. These lipid nanoparticles have high transfection efficiency without additional cytotoxicity. In another embodiment, a low molecular weight pentaethylenehexamine (PEHA) is conjugated to human serum albumin via cross linking agents, resulting in a hyper-cationized pH-responsive APC, also referred to herein as HSA-PEHA. For HSA-PEHA, the PEHA-to-HSA ratio is between 1 and 30, preferably 5-20, even more preferably 8-15, even more preferably between 10-12. When incorporated into a nanoparticle, the resulting formulation that includes the lipid nanoparticle and the incorporated hyper-cationized pH-responsive conjugate such as HSA-PEHA is referred to herein as a lipid-coated albumin nanoparticle (LCAN). An exemplary LCAN is a lipid coated albumin nanoparticles which is composed of DOTAP/sPC/TPGS/HSA-PEHA.

LCANs are especially useful for the delivery of NAs, such as antisense oligonucleotides, pDNAs, siRNAs, shRNAs, miR5, and anti-miR5. Without wishing to be bound by theory, it is believed HSA-PEHA improves the stability and biological activity of the nanoparticles. In certain embodiments, the lipids in this formulation are DOTAP, SPC, and TPGS. In some embodiments, the ratio of DOTAP:SPC:TPGS is about 25:70:5 (m/m). In exemplary embodiments, the weight ratio of total lipids-to-HSA-PEHA is between 20 and 1, for example, between 15 and 2, or between 12.5 and 2.5.

Targeting Agents

The addition of targeting agents to the LN can provide increased efficacy over passive targeting approaches. Targeting involves incorporation of specific targeting moieties such as, but not limited to, ligands or antibodies, cell surface receptors, peptides, lipoproteins, glycoproteins, hormones, vitamins, antibodies, antibody fragments, prodrugs, and conjugates or combinations of these moieties. Some non-limiting examples of targeting agents include folate, cRGD (e.g., cyclo(Arg-Gly-Asp-D-Phe-Cys) (RGDfC)) peptides, galactose-containing moieties, transferrin, EPPT1 peptide, low density lipoprotein, epidermal growth factors, and antibodies. cRGD can refer to any derivative of or related cRGD peptide, for example, cRGDfC, cRGDfK, cRGDfE, etc. In exemplary embodiments, the cRGD peptide is cRGDfC (cyclo(Arg-Gly-Asp-D-Phe-Cys)). In some embodiments, maximization of targeting efficiency can be achieved by surface coating the LN with an appropriate targeting moiety rather than encapsulation of the targeting agent. This method can optimize interaction of the LN with cell surface receptors. Targeting agents may be either directly incorporated into the LN during synthesis or added in a subsequent step. Functional groups on the targeting moiety as well as specifications of the therapeutic application (e.g., degradable linkage) can help in determining the appropriate means of incorporation into the LN. Targeting moieties that do not have lipophilic regions cannot readily insert into the lipid bilayer of the LN directly and may require prior conjugation to lipids before insertion or may form an electrostatic complex with the LNs. Under certain circumstances, a targeting ligand may not be capable of directly binding to a lipophilic anchor. In these circumstances, a molecular bridge in the form of a crosslinking agent may be utilized to facilitate the interaction. A crosslinking agent can be useful in situations where steric restrictions of the anchored targeting moiety prevent sufficient interaction with the intended physiological target. Additionally, if the targeting moiety is only functional under certain orientations (e.g., monoclonal antibody), linking to a lipid anchor via cross-linking agent may be beneficial. Traditional methods of bioconjugation may be used to link targeting agents to LNs.

Reducible or hydrolysable linkages may be applied to prevent accumulation of the formulation in vivo and subsequent cytotoxicity.

In exemplary embodiments of the present application, RGD (or cRGD) or folate targeting agent is incorporated as a targeting conjugate, for example, folate-PEG-CHEMS (folate-polyethylene glycol-cholesteryl hemisuccinate) or folate-PEG-DSPE (folate-polyethylene glycol-distearoyl phosphatidylethanolamine) or cRGDfC-PEG-DSPE (cyclo (RGDfC)-polyethylene glycol-distearoyl phosphatidylethanolamine). In some targeting conjugates, a minimum of 5 mole % of the conjugate contains a targeting agent. In some embodiments, the conjugate includes at least about 50 mole %, at least about 80 mole %, at least about 90 mole %, or at least about 95 mole % of the targeting agent. In other exemplary embodiments, the conjugate includes about 50 mole %, about 80 mole %, about 90 mole %, or about 95 mole % of the targeting agent. In exemplary embodiments, the mole percent of targeting conjugate among total lipids is about 0.05 to 20 mole %, for example about 0.5 to 5 mole %.

Therapeutic Agents

A wide spectrum of therapeutic or diagnostic agents may be used in conjunction with the LNs described herein. Non-limiting examples of such therapeutic and diagnostic agents include nucleic acids, proteins, polysaccharides, lipids, radioactive substances, therapeutic agents, prodrugs, and combinations thereof. Therapeutic agents include, but are not limited to, antineoplastic agents, anti-infective agents, local anesthetics, anti-allergics, antianemics, angiogenesis, inhibitors, beta-adrenergic blockers, calcium channel antagonists, anti-hypertensive agents, anti-depressants, anti-convulsants, anti-bacterial, anti-fungal, anti-viral, anti-rheumatics, anthelminithics, antiparasitic agents, corticosteroids, hormones, hormone antagonists, immunomodulators, neurotransmitter antagonists, anti-diabetic agents, anti-epileptics, anti-hemmorhagics, anti-hypertonics, antiglaucoma agents, immunomodulatory cytokines, sedatives, chemokines, vitamins, toxins, narcotics, imaging agents, and combinations thereof.

Nucleic acid-based therapeutic agents are highly applicable to the LN formulations of the present disclosure. Examples of such nucleic acid-based therapeutic agents include, but are not limited to: pDNA, siRNA, miRNA, anti-miRNA, antisense oligonucleotides (ASO), and combinations thereof. To protect from serum nucleases and to stabilize the therapeutic agent, modifications to the substituent nucleic acids and/or phosphodiester linker can be made. Such modifications include, but are not limited to: backbone modifications (e.g., phosphothioate linkages); 2' modifications (e.g., 2'-O-methyl substituted bases); zwitterionic modifications (6'-aminohexy modified ODNs); the addition of a lipophilic moiety (e.g., fatty acids, cholesterol, or cholesterol derivatives); and combinations thereof.

In an exemplary embodiment of the invention, the therapeutic agent is an ASO targeted to a portion of a nucleic acid encoding Akt-1, and which modulates the expression of Akt-1. The oligonucleotide compounds are designed to specifically hybridize with one or more nucleic acids encoding Akt-1. Such ASOs are disclosed in U.S. Pat. No. 7,122,527, the contents of which are hereby incorporated by reference in their entirety. One exemplary ASO, RX-0201 (Archexin®) which is a 20-mer phosphorothioate antisense oligonucleotide, is targeted to a site in the coding region of the Akt-1 gene having the following sequence: 5' cgccaagga-gatcatgcagc 3' at site 1,478 of Akt-1 gene (Seq. Id. No.: 3). The sequence for the backbone of RX-0201 is complementary to this site.

Another ASO, RX-0194, is targeted to a site on the Akt-1 gene having the following sequence: 5' agtggactg-gtggggctgg 3' at site 1,271 of Akt-1 gene (Seq. Id. No.: 4). The sequence for the backbone of RX-0194 is complementary to this site. Oligomers comprising either 5 or 10 nucleotide upstream and downstream from the sequence where the 20-mer of RX-0194 was derived showed a measurable inhibition of Akt-1 mRNA expression. The truncated versions of RX-0194 and RX-0201 also showed an inhibition of cancer cell proliferation. In addition to the above 2 ASOs, five additional antisense oligonucleotide compounds which down-regulate Akt-1 mRNA expression and cause cytotoxic effects on cancer cell lines include:

RX-0616, comprising 5' agatagctggtgacagacag 3' (Seq. Id. No.: 5) hybridizable to the site beginning at position 2101 of Akt-1 gene, having the following sequence: 5' ctgtctgtcac-cagctatct 3' (Seq. Id. No.: 6);

RX-0627, comprising 5' cgtggagagatcatctgagg 3' (Seq. Id. No.: 7) hybridizable to the site beginning at position 2473 of Akt-1 gene, having the following sequence: 5' cctcagat-gatctctccacg 3' (Seq. Id. No.: 8);

RX-0628, comprising 5' tcgaaaaggtcaagtgctac 3' (Seq. Id. No.: 9) hybridizable to the site beginning at position 2493 of Akt-1 gene, having the following sequence: 5' gtagcacttgac-cttttcga 3' (Seq. Id. No.: 10);

RX-0632, comprising 5' tggtgcagcggcagcggcag 3' (Seq. Id. No.: 11) hybridizable to the site beginning at position 2603 of Akt-1 gene, having the following sequence: 5' ctgccgctgccgctgcacca 3' (Seq. Id. No.: 12); and RX-0638, comprising 5' ggcgcgagcgcgggcctagc 3' (Seq. Id. No.: 2) hybridizable to the site beginning at position site 170 of Akt-1 gene, having the following sequence: 5' gctag-gcccgcgctcgcgcc 3' (Seq. Id. No.: 13).

In other embodiments, the therapeutic agent is an ASO targeted to a portion of a nucleic acid encoding HIF-1, and which modulates the expression of HIF-1. The oligonucleotide compounds are designed to specifically hybridize with one or more nucleic acids encoding HIF-1. Such ASOs are disclosed in U.S. Pat. No. 7,205,283, the contents of which are hereby incorporated by reference in their entirety. An exemplary ASO, RX-0047, a 20-mer phosphorothioate antisense oligonucleotide comprising 5' aatgagccaccagtgtccaa 3' (Seq. Id. No.: 2) is a potent inhibitor of "Hypoxia inducible factor-1 alpha" (HIF-1α) and is targeted to a site on the HIF-1 gene having the following sequence: 5' ttggacactg-gtggctcatt 3' at site 2,772 of HIF-1 gene (Seq. Id. No.: 14). The sequence for the backbone of RX-0047 is complementary to this site. Another exemplary ASO according to this embodiment, RX-0149, comprising 5' ggagctaacatctccaagtc 3' (Seq. Id. No.: 15), is targeted to a site in the coding region of the HIF-1 gene having the following sequence: 5' gact-tggagatgttagctcc 3' at site 1,936 of HIF-1 gene (Seq. Id. No.: 16). The sequence for the backbone of RX-0149 is complementary to this site. Oligomers comprising either 5 or 10 nucleotides upstream and downstream from the sequence where the 20-mer of RX-0047 and RX-0149 were derived showed a measurable inhibition of HIF-1 mRNA expression and an inhibition of proliferation of cancer cells. The truncated versions of RX-0047 and RX-0149 which showed some inhibition of HIF-1 mRNA expression also showed an inhibition of cancer cell proliferation.

The present invention includes other oligomeric antisense compounds, including but not limited to oligonucleotide mimetics. The antisense compounds can include from about 10 to about 30 nucleobases, for example, oligonucleotides having about 20 nucleobases (i.e. about 20 linked nucleosides). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

Applications

Depending on the application, the lipid nanoparticles disclosed herein may be designed to favor characteristics such as increased interaction with nucleic acids, increased serum stability, lower RES-mediated uptake, targeted delivery, or pH sensitive release within the endosome. Because of the varied nature of LN formulations, any one of the several methods provided herein may be applied to achieve a particular therapeutic aim. Cationic lipids, anionic lipids, PEG-lipids, neutral lipids, fusogenic lipids, cationic polymers, anionic polymers, polymer conjugates, peptides, targeting moieties, and combinations thereof may be applied to meet specific aims.

The lipid nanoparticles described herein can be used as platforms for therapeutic delivery of oligonucleotide (ON) therapeutics, such as cDNA, siRNA, shRNA, miRNA, anti-miR, and antisense oligonucleotides (ASO). This therapeutics could be used to manage a wide variety of diseases such as various types of cancers, leukemias, viral infections, and other diseases. The particular disease treatable according to the invention depends, of course, upon the therapeutic agent incorporated into the LN of the invention. The invention is particularly suitable for encapsulation of nucleic acids, for example antisense oligonucleotides. Nucleic acids, and in particular antisense nucleotides are especially useful for the treatment of tumors and cancers. Examples of tumors and cancers treatable according to the invention include, for example Brain cancer, bladder cancer, lung cancer, breast cancer, melanoma, skin cancer, epidermal carcinoma, colon and rectal cancer, non-Hodgkin lymphoma, endometrial cancer, pancreatic cancer, kidney (renal cell) cancer, prostate cancer, leukemia thyroid cancer, head and neck, ovarian cancer, hepatocellular cancer, cervical cancer, sarcomas, gastric cancers, multiple myeloma, lymphomas, and gastrointestinal cancer, and uterine cancer. Specific examples include epidermal carcinoma, pancreatic cancer and breast cancer.

A number of tumors overexpress receptors on their cell surface. Targeting moieties such as cRGD peptides, folate, transferrin (Tf), antibodies low density lipoprotein (LDL), and epidermal growth factors can greatly enhance activity by enabling targeted drug delivery. Multi-targeted systems are another possibility and may be applied further to specify a particular target cell subtype.

Implementation of embodiments of the LN formulations described herein alone or in combination with one another synergizes with current paradigms of lipid nanoparticle design.

Depending on the therapeutic application, the LNs described herein may be administered by the following methods: peroral, parenteral, intravenous, intramuscular, subcutaneous, intraperitoneal, transdermal, intratumoral, intraarterial, systemic, or convection-enhanced delivery. In particular embodiments, the LNs are delivered intravenously, intramuscularly, subcutaneously, or intratumorally. Subsequent dosing with different or similar LNs may occur using alternative routes of administration.

Pharmaceutical compositions of the present disclosure comprise an effective amount of a lipid nanoparticle formulation disclosed herein, and/or additional agents, dissolved or dispersed in a pharmaceutically acceptable carrier. The phrases "pharmaceutical" or "pharmacologically acceptable" refers to molecular entities and compositions that produce no adverse, allergic or other untoward reaction when administered to an animal, such as, for example, a human. The preparation of a pharmaceutical composition that contains at least one compound or additional active ingredient will be known to those of skill in the art in light of the present disclosure, as exemplified by Remington's Pharmaceutical Sciences, 2003, incorporated herein by reference. Moreover, for animal (e.g., human) administration, it will be understood that preparations should meet sterility, pyrogenicity, general safety and purity standards as required by FDA Office of Biological Standards.

A composition disclosed herein may comprise different types of carriers depending on whether it is to be administered in solid, liquid or aerosol form, and whether it need to be sterile for such routes of administration as injection. Compositions disclosed herein can be administered intravenously, intradermally, transdermally, intrathecally, intraarterially, intraperitoneally, intranasally, intravaginally, intrarectally, topically, intramuscularly, subcutaneously, mucosally, in utero, orally, topically, locally, via inhalation (e.g., aerosol inhalation), by injection, by infusion, by continuous infusion, by localized perfusion bathing target cells directly, via a catheter, via a lavage, in creams, in lipid compositions (e.g., liposomes), or by other method or any combination of the forgoing as would be known to one of ordinary skill in the art (see, for example, Remington's Pharmaceutical Sciences, 2003, incorporated herein by reference).

The actual dosage amount of a composition disclosed herein administered to an animal or human patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a composition herein and/or additional agents is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier.

In further embodiments, a composition described herein may be administered via a parenteral route. As used herein, the term "parenteral" includes routes that bypass the alimentary tract. Specifically, the pharmaceutical compositions disclosed herein may be administered, for example but not limited to, intravenously, intradermally, intramuscularly, intraarterially, intrathecally, subcutaneous, or intraperitoneally (U.S. Pat. Nos. 6,753,514, 6,613,308, 5,466,468, 5,543,158; 5,641,515; and 5,399,363 are each specifically incorporated herein by reference in their entirety).

Solutions of the compositions disclosed herein as free bases or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption such as, for example, aluminum monostearate or gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety, and purity standards as required by FDA Office of Biologics standards.

Sterile injectable solutions are prepared by incorporating the compositions in the required amount in the appropriate solvent with various other ingredients enumerated above, as required, followed by filtered sterilization. Generally, dispersions are prepared by incorporating the various sterilized compositions into a sterile vehicle which contains the basic dispersion medium and the required other ingredients from those enumerated above. In the case of sterile powders for the preparation of sterile injectable solutions, some methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

In other embodiments, the compositions may be formulated for administration via various miscellaneous routes, for example, topical (i.e., transdermal) administration, mucosal administration (intranasal, vaginal, etc.) and/or via inhalation.

Pharmaceutical compositions for topical administration may include the compositions formulated for a medicated application such as an ointment, paste, cream or powder. Ointments include all oleaginous, adsorption, emulsion and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the composition and provide for a homogenous mixture. Transdermal administration of the compositions may also comprise the use of a "patch." For example, the patch may supply one or more compositions at a predetermined rate and in a continuous manner over a fixed period of time.

In certain embodiments, the compositions may be delivered by eye drops, intranasal sprays, inhalation, and/or other aerosol delivery vehicles. Methods for delivering compositions directly to the lungs via nasal aerosol sprays has been described in U.S. Pat. Nos. 5,756,353 and 5,804,212 (each specifically incorporated herein by reference in their entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts and could be employed to deliver the compositions described herein. Likewise, transmucosal drug delivery in the form of a polytetrafluoroetheylene support matrix is described in U.S. Pat. No. 5,780,045 (specifically incorporated herein by reference in its entirety), and could be employed to deliver the compositions described herein.

It is further envisioned the compositions disclosed herein may be delivered via an aerosol. The term aerosol refers to a colloidal system of finely divided solid or liquid particles dispersed in a liquefied or pressurized gas propellant. The typical aerosol for inhalation consists of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

EXAMPLES

Example 1. Preparation of Liposomal Formulation and LCAN Formulation

1. Preparation and Characterization of Liposomal Formulation for Antisense Oligonucleotides Liposomal formulation for RX-0047 (L-RX-0047) was prepared by an ethanol diffusion method. Lipids composition was DOTAP/DOPE/TPGS or DOTAP/soyPC/TPGS at molar ratio of 45:50:5. Briefly, lipids were dissolved in ethanol with or without PEI2K, i.e. PEI having a molecular weight of about 2000. The ratio for lipids-to-PEI2K was 12.5:1. RX-0047 was dissolved in citrate buffer (20 mM, pH 4) and then added into lipids solution or lipids/PEI2K solution under vortexing to spontaneously form pre-liposomes at an ethanol concentration of 40% (v/v). The weight ratio for RX-0047 to lipids was 12.5:1. The complexes were then dialyzed against citrate buffer (20 mM, pH 4) at room temperature for 2 h and then against HEPES buffered saline (HBS, 20 mM HEPES, 145 mM NaCl, pH 7.4) overnight at room temperature, using a MWCO 10 000 Dalton Spectra/Por Float-A-Lyzer instrument (Spectrum Laboratories, Rancho Dominguez, Calif.) to remove free RX-0047.

Folate targeted liposomal formulation for RX-0047 (F-L-RX-0047) was prepared by the same method as described above. The liposomes were composed with DOTAP/sPC/TPGS/F-PEG-CHEMS at molar ratio of 45/50/4.5/0.5 or 45/50/4/1.

RGD targeted liposomal formulation for RX-0047 (cRGD-L-RX-0047) was prepared by the same method as described above. The liposomes were composed with DOTAP/sPC/TPGS/cRGD-PEG-DSPE at molar ratio of 45/50/4.5/0.5 or 45/50/4/1

2. Synthesis of HSA-PEHA Conjugate

HSA-PEHA conjugates were synthesized by activation of carboxyls on HSA with EDC and forming amide linkages with amines on PEHA. The HSA:PEHA:EDC molar ratio used during synthesis was 1:1500:200 (mol/mol). HSA (25%, Purchased from Octapharma) was conjugated to pentaethylenehexamine (PEHA, purchased from Sigma-Aldrich) by reacting HSA with a large excess of PEHA in the presence of 1-ethyl-3-(3-dimethylamino)-propylcarbodiimide (EDC) and sulfo-N-hydroxysuccinimide in 50 mM borate buffer or water at pH 8.0. Briefly, 5 g of PEHA (MW 232.37, technical grade) was dissolved in 80 mL of ddH$_2$O and then adjusted to pH 8.0 using 1 M HCl. 1 g (4 mL) of HSA and then 562.5 mg of 1-ethyl-3-[3-dimethylaminopropyl]carbodiimide (EDC, dissolved in DMSO) were added into the PEHA solution under stirring. The reaction continued for 3-4 h at room temperature. The HSA-PEHA product was purified by gel membrane chromatography on a PD-10 desalting column or by dialysis using MWCO 10,000 Spectrum membrane against ddH$_2$O (doubly distilled water) at 4° C. to remove unreacted PEHA and byproducts. The dialysis buffer was replaced every 3-4 h until amines from PEHA became undetectable by the standard ninhydrin or trinitrobenzenesulfonic acid (TNBS) amine essay in the external buffer at the 3 h time point at the end of the dialysis cycle. For scaled-up synthesis, the dialysis procedure should be replaced by tangential flow diafiltration, e.g., using a Millipore Pellicon cassette system or a Spectropor hollowfiber system. This method can also be used to concentrate the product to a desirable concentration. The product was passed through a 0.22 μm sterile filter into a sterile container and stored at 4° C. For long-term storage, the product can be stored at −20° C. The product can also be lyophilized.

The product protein concentration was determined by BCA protein assay and the PEHA content in the product was determined by TNBS amine content assay using a PEHA-based standard curve. The molecular weight of the HSA-PEHA conjugate was determined by matrix-assisted laser desorption-ionization time-of-flight mass spectrometry (MADLI TOF MS). On average, there were 11 PEHA linked to each HSA based on the result showing m/z of 66405.756. SDS-PAGE analysis showed that the conjugate migrated as a single band, indicating lack of intermolecular crosslinking in the HSA-PEHA product.

3. Synthesis of cRGDfC-PEG-DSPE Conjugate cRGDfC (Cyclo(Arg-Gly-Asp-D-Phe-Cys)) and PEG-DSPE-maleimide was conjugated via -SH and -maleimide reaction resulting in a thioether linkage. The cRGDfC and PEG-PSPE-maleimide molar ratio used during the reaction was 1.5:1. The cRGDfC and PEG-DSPE solutions dissolved each in PBS buffer containing 5 mM EDTA (pH=7.0) were combined and reacted at room temperature for 6 h with stirring. The product was purified by gel filtration on a PD-10 column to remove unreacted/excess cRGDfC from the product. For scaled-up reactions, the gel filtration can be replaced with GPC, dialysis using MWCO 2000 membrane, or tangential flow diafiltration. The product can be frozen or lyophilized for long-term stability. The product purity was confirmed by HPLC and by LC-MS. Minimum cRGDfC conjugation level (e.g., 80%) and free peptide content (e.g., <1%) can be established as specifications. The cRGDfC content in the product can be determined by BCA protein assay.

4. Synthesis of Folate-PEG-DSPE Conjugate

Ten mg of Folic acid was reacted with 7 mg of N,N'-dicyclohexylcarbodiimide (DCC) and 2.87 mg of N-hydroxysuccinimide (NHS) in DMSO (0.5 ml) with a small amount of triethylamine (20 µl) at molar ratios of folate/DCC/NHS=1/1.5/1.1 for 3 hr at room temperature. The reaction mixture was centrifuged to remove byproduct dicyclohexylurea. 77 mg of DSPE-PEG-amine was dissolved in DMSO (0.5 ml) with a small amount of triethylamine (20 µl) and then reacted with folate-NHS synthesized above at molar ratio of 1:1 for 3 hr at room temperature. Folate-PEG-DSPE was purified by precipitation with 10× volume acetone. The precipitate was collected by centrifugation and then dried under vacuum. The product was further purified by dialysis against ddH$_2$O using a MWCO 2000 membrane, followed by lyophilization. Product purity was confirmed by HPLC. Minimum folate conjugation level (e.g., 80%) relative to all PEGylated lipid and undetectable free folate content were established as specifications. The folate content in the product was determined by UV spectrometry at 371 nm or by HPLC.

5. Synthesis of Folate-PEG-DSPE Conjugate

The synthesis of folate-PEG-CHEMS was performed by reacting folate-PEG-amine with CHEMS-NHS. Both folate-PEG-amine and CHEMS-NHS were synthesized by method described previously (Xiang et al., Int J. Pharm., 356 (2008) 29-36). Briefly, for synthesis of folate-PEG-bis-amine, folic acid (26.5 mg) and PEG-bis-amine (167.5 mg) were dissolved in 1 mL DMSO. Then, 8.6 mg of NHS and 15.5 mg of DCC were added to the solution, and the reaction was allowed to proceed overnight at room temperature. The product, folate-PEG-amine, was then purified by Sephadex G-25 gel-filtration chromatography. For synthesis of CHEMS-NHS, CHEMS (1 g) was reacted with 475 mg NHS and 1.25 g DCC in tetrahydrofuran overnight at room temperature. The product CHEMS-NHS was purified by recrystallization. Finally, for synthesis of F-PEG-CHEMS, folate-PEG-amine (137 mg, 40 µmol) and CHEMS-NHS (29.2 mg, 50 µmol) were dissolved in CHCl$_3$ (50 mL), and reacted overnight at room temperature. The solvent (CHCl$_3$) was then removed by rotary evaporation and the residue was hydrated in 50 mM Na$_2$CO$_3$ (10 mL) to form F-PEG-CHEMS micelles. The micelles were then dialyzed against deionized water using a Spectrum dialysis membrane with a molecular weight cut-off (MWCO) of 14 kDa to remove low molecular weight by-products. The product F-PEG-CHEMS was then dried by lyophilization, which yielded a yellow powder product (130 mg) with a yield of 76.5%. The identity of the product was confirmed by thin-layer chromatography (TLC) and by $^1$H NMR in DMSO-d$_6$.

6. Preparation and Characterization of LCAN Formulation for Antisense Oligonucleotides Lipid coated albumin nanoparticles (LCAN) were prepared by ethanol dilution method. Lipids 1,2-dioleoyl-3-trimethylammonium-propane (DOTAP) (Avanti Polar Lipids), L-α-phosphatidylcholine derived from soybean (SPC) (Avanti Polar Lipids), and d-alpha-tocopheryl polyethylene glycol 1000 succinate (TPGS) (Eastman Chemical) were dissolved in ethanol. Lipids were combined at 25:70:5 (mol/mol). HSA-PEHA was mixed with lipid solution at weight ratio of 12.5:3. The composition of antisense/total lipid/HSA-PEHA weight ratio was 1:10:3. Briefly, HSA-PEHA in Hepes buffer (20 mM, pH 7.4) and lipids dissolved in EtOH were mixed under vortexing and resulting EtOH concentration was 60%. RX-0047 or RX-0201 was dissolved in Hepes buffer (20 mM, pH 7.4) and then added into lipids and HSA-PEHA solution under vortexing to spontaneously form pre-LCAN at an EtOH concentration of 40% (v/v). The complexes were then dialyzed against Hepes buffer (20 mM, pH 7.4) at room temperature for 2 h and then against HEPES buffered saline (HBS, 20 mM HEPES, 145 mM NaCl, pH 7.4) overnight at room temperature, using a MWCO 10 000 Dalton Snakeskin dialysis tubing to remove free ASO.

The LCAN formulation was concentrated to 20-fold and then washed with Hepes buffer (5 mM, pH 7.4) to remove NaCl. The product was diluted to the desired concentration and 10% sucrose was added. The final products were then filtered through a 0.45 µm filter and then stored at −70° C.

7. Preparation and Characterization of Targeted LCAN Formulation for Antisense Oligonucleotides RGD targeted LCAN formulation was prepared by the similar method as described in Example 5. For the RGD targeted LCAN formulation, the lipids were composed with DOTAP/soyPC/TPGS/cRGDfC-PEG-DSPE at molar ratio of 25:70:4:1 and the composition of antisense/total lipid/HSA-PEHA weight ratio was 1:10:3. The lipid mixture containing a targeting agent was made by mixing DOTAP, soyPC, TPGS and cRGDfC-PEG-DSPE as a ratio of 25:70.4:1. The lipid mixture components in 60% ethanol (Solution A) were combined with an equal volume of HSA-PEHA in 20% ethanol (Solution B) by two-pumps and a Y-connector to yield a solution of 40% ethanol (Solution C). RX-0201 (Archexin®) was dissolved in HEPES buffer (20 mM, pH 7.4) with 40% ethanol to form Solution D. Solution C and Solution D in equal volume were combined by two-pumps and a Y-connector to yield a solution of 40% ethanol (Solution E) and Solution E was diluted four times with ddH$_2$O to 10% ethanol under stirring. To the Solution E, equal volume of 0.5 M NaCl was added to produce 250 mM NaCl and 5% ethanol concentration in the solution (Solution F). The RGD targeted LCAN product Solution F was purified by tangential flow diafiltration, MWCO 30 kDa membrane in which included the concentration of the Solution F to 0.5 mg/mL in RX-0201 concentration as a first, diafiltration against 5 mM phosphate buffer (pH 7.4) until the RX-0201 concentration in the permeate solution drops below 10 µg/mL as a second step and the concentration of the product to 2.5 mg/mL in RX-0201 concentration as a final step. To the product, ¼ volume of 50% sucrose was added to produce a solution of 10% sucrose and filtered through a 0.22 µm sterile filter; use pre-filtration if necessary. For the lyophilization, under sterile conditions the filtered product (10 mL) was transferred into 50 mL vials, frozen and lyophilized using a 2-stage program: shelf cool to 0° C., cool 0.5° C./min to −40° C., reduce pressure to 0.12-0.16 atm, 30 h primary drying at −25° C. Heat to 25° C. at 5° C./min, 6 h maximum vacuum drying. The final cRGD targeted LCAN product was stored at 4° C. and reconstituted with water for injection at the time of use.

Other targeted LCAN products such as folate-LCAN-RX-0201, cRGD-LCAN-RX-0047 and folate-LCAN-RX-0047) were prepared by the same method as described above.

Example 2. Characterization of Liposomal Formulation and LCAN Formulation

RGD targeted liposomal formulation was composed with DOTAP/sPC/TPGS/cRGDfC-PEG-DSPE at molar ratio of 45/50/4.5/0.5 or 45/50/4/1. The particle size and zeta potential were shown in Table 1. cRGDfC-PEG-DSPE concentration did not change liposome particle size and zeta potentials.

TABLE 1

Characterization of RGD targeted liposomal formulation

| Formulation | Particle size (nm) | Zeta potentials (mV) |
|---|---|---|
| DOTAP/sPC/TPGS/cRGDfC-PEG-DSPE (45/50/4.5/0.5) | 91.3 ± 4.3 | 18.8 ± 1.3 |
| DOTAP/sPC/TPGS/cRGDfC-PEG-DSPE (45/50/4.0/1.0) | 90.2 ± 6.2 | 20.4 ± 2.1 |

Drug loading efficiency in LCAN products was at 2 mg/mL as an oligonucleotide concentration, determined by OliGreen ssDNA quantitation reagent (Invitrogen) as shown in Table 2. The percent recovery of oligonucleotide in the product was 60 to 76%. The particle size of LCAN products was analyzed on a NICOMP Particle Sizer Model 370 (Particle Sizing Systems, Santa Barbara, Calif.) and ranged 92.7 to 124 nm. A volume-weighted Gaussian distribution analysis was used to determine the mean particle diameter and size distribution. The zeta potential (ξ) was determined on a ZetaPALS (Brookhaven Instruments Corp., Worcestershire, N.Y.). All measurements were carried out in triplicate. The zeta potential was between 14.5 and 29.4 mV.

TABLE 2

Characteristics of LCAN nanoparticles with RX-0201 or RX-0047

| Formulations | Conc. (mg/ml) | Particle size (nm) | Zeta potential (mV) | Encapsulation Efficiency (%) |
|---|---|---|---|---|
| LCAN-RX-0201 | 2.0 ± 0.2 | 97.4 ± 4.5 | 29.4 ± 3.2 | 72.6 ± 7.8 |
| Folate-LCAN-RX-0201 | 2.0 ± 0.1 | 92.7 ± 6.5 | 25.3 ± 2.4 | 70.7 ± 6.3 |
| cRGDfC-LCAN-RX-0201 | 2.0 ± 0.3 | 102.5 ± 10.3 | 26.5 ± 4.8 | 68.4 ± 5.6 |
| LCAN-RX-0047 | 2.0 ± 0.1 | 113.7 ± 7.8 | 25.4 ± 3.8 | 76.2 ± 6.9 |
| Folate-LCAN-RX-0047 | 2.0 ± 0.2 | 117.9 ± 11.3 | 14.5 ± 2.0 | 62.1 ± 7.6 |
| cRGDfC-LCAN-RX-0047 | 2.0 ± 0.2 | 123.8 ± 8.5 | 20.9 ± 2.2 | 60.0 ± 5.9 |
| LCAN-Control | — | 80.0 ± 7.0 | 46.2 ± 6.6 | — |

Example 3. Freeze and Thaw Stability and Lyophilization

Two different batches of liposomal formulation were synthesized. Particle sizes, zeta potential and RX-0047 content were measured before and after a cycle of freeze-thaw. For lyophilization, each vial containing 5 ml LCAN formulation was lyophilized in a LABCONCO lyophilizer. There are three stages in the complete drying process: freezing, primary drying, and secondary drying. After secondary drying, vials were stored at 4° C. or product were suspend with ddH$_2$O to check the particles size, zeta potential and drug content.

The stability at 4° C. and freeze-thaw stability was evaluated. As shown in Table 3, the particle size and zeta potential were slightly, but not significantly, increased after stored two week at 4° C. After repeat freeze-thaw process three times, the particle size and zeta potential were not significantly change between before and after the freeze-thawing (Table 3).

TABLE 3

Stability of LCAN-RX-0047 at 4° C. and after freeze-thawing

| Parameters | Initial values | After two weeks at 4° C. | After freeze/thaw One time | Two times | Three times |
|---|---|---|---|---|---|
| Particle size (nm) | 97.8 ± 5.3 | 106.9 ± 4.9 | 93.2 ± 2.8 | 91.5 ± 5.2 | 92.0 ± 3.2 |
| Zeta potential (mV) | 29.2 ± 2.41 | 32.8 ± 0.7 | 27.3 ± 0.9 | 30.0 ± 0.6 | 29.3 ± 1.41 |
| Drug content (mg/ml) | 0.98 ± 0.25 | 0.92 ± 0.21 | 0.92 ± 0.06 | 0.98 ± 0.12 | 0.95 ± 0.15 |

Example 4. Biological Tests 1. mRNA and Protein Down-Regulation by Liposomal Formulation and LCAN Formulation in Cancer Cells KB (human epidermal carcinoma), PANC-1 (human pancreas) and MDA-MB-435 (human breast) cells were used to gene down-regulation studies. KB cells were grown in RPMI1640 medium containing 10% heat-inactivated fetal bovine serum (FBS), 2 mM L-glutamine, 100 U/ml penicillin and 100 mg/ml streptomycin. PANC-1 and MDA-MB-435 cells were grown in DMEM medium containing 10% heat-inactivated fetal bovine serum (FBS), 2 mM L-glutamine, 100 U/ml penicillin and 100 mg/ml streptomycin. Cells were maintained in a humidified incubator at 37° C. in 5% CO$_2$.

Cells were plated at a density of 2×10$^5$ cells/well into 6-well plates and cultured overnight. Cells were transfected with L-RX-0047 or F-L-RX-0047 or cRGDfC-L-RX-0047 for 4 h at 37° C. For receptor blocking studies, 100 uM of folic acid or cRGDfC was added to media during F-L-RX-0047 or cRGDfC-L-RX-0047 exposure. After transfection, the medium was replaced with fresh growth medium and the cells were incubated for 48 h at 37° C. under 5% CO$_2$ atmosphere. Then cells were collected and analyzed for HIF-1α mRNA level by real-time qRT-PCR and for HIF-1α protein (nuclear protein) expression by western blot analysis.

HIF-1α mRNA down-regulation by treatment of L-RX-0047 or cRGDfC-L-RX-0047 was determined by real-time RT-PCR (FIG. 1) at 0.25 μM of RX-0047 concentration. The results showed that cRGDfC-L-RX-0047 decreased HIF-1α mRNA expression in MDA-MB-435 cells. cRGDfC-L-RX-0047 with 1.0% of cRGDfC showed more HIF-1α mRNA down-regulation compared to cRGDfC-L-RX-0047 with 0.5% cRGDfC. Both cRGDfC targeted RX-0047 formulations caused more decrease of HIF-1α mRNA expression also compared to non-targeted L-RX-0047. Moreover, HIF-1α down-regulation effect was blocked by addition of 1 mM of cRDGfC (FIG. 1). These results indicated that cRGDfC-L-RX-0047 selectively target tumor cells via αvβ3 integrin receptor.

Figure 2:
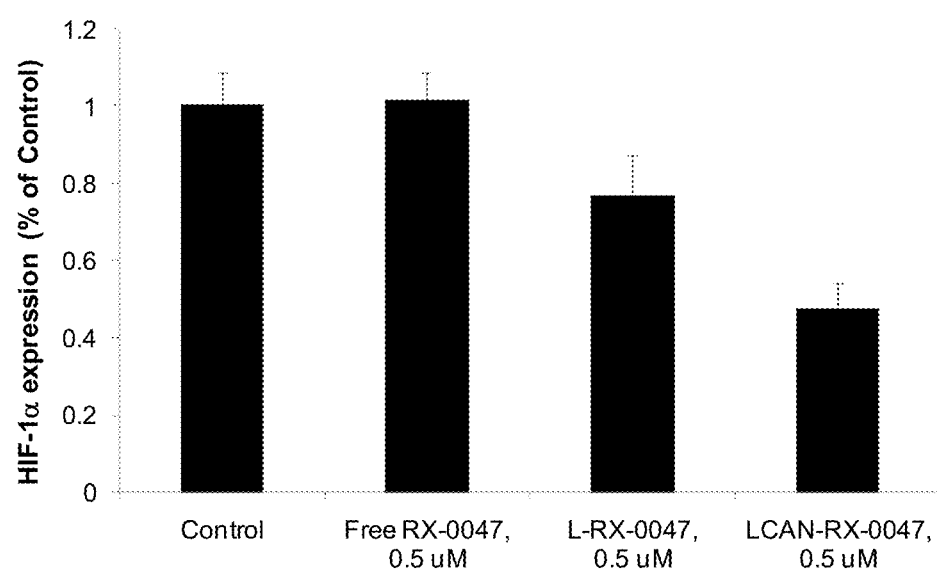
FIG. 2 illustrates HIF-1α mRNA expression in KB cells upon treatment with free RX-0047, L-RX-0047 and LCAN-RX-0047.

In vitro gene targeting efficiency of LCAN formulation was determined by real-time RT-PCR. In KB cells, LCAN-RX-0047 significantly decreased HIF-1α mRNA expression compared to liposomal formulation containing RX-0047 (L-RX-0047) at 0.5 μM of RX-0047 concentration (FIG. 2). Also, L-RX-0047 showed significant HIF-1α mRNA down-regulation compared to free RX-0047 or control group.

Figure 3:
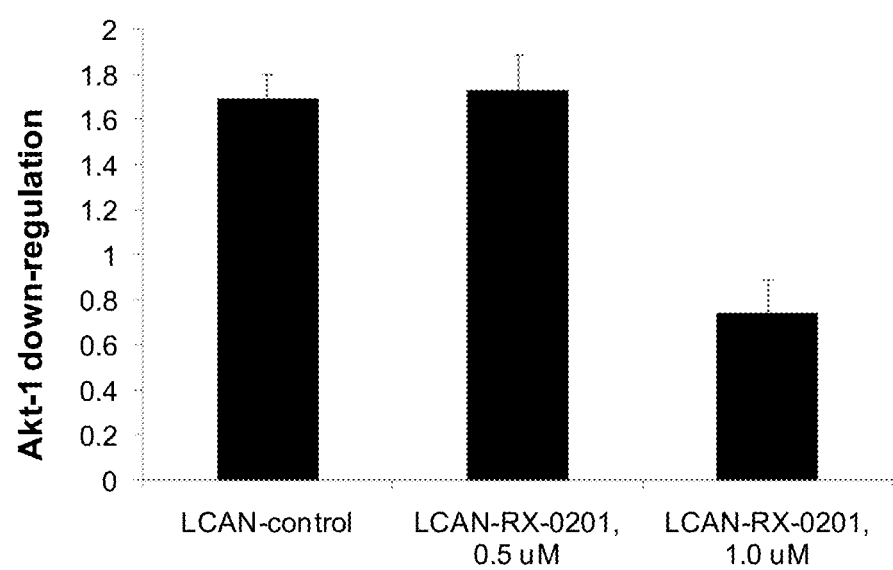
FIG. 3 illustrates Akt-1 mRNA down-regulation in KB cells upon treatment with LCAN-RX-0201.
Figure 4:
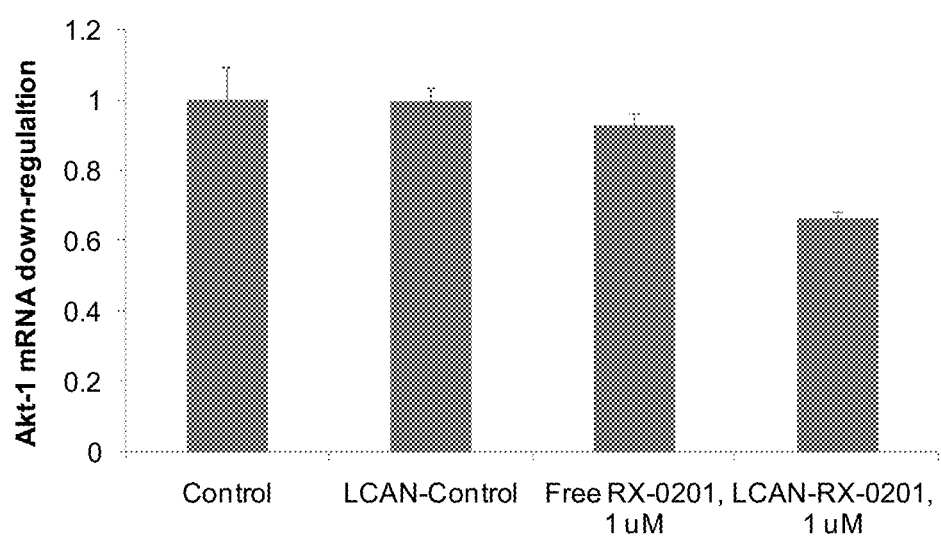
FIG. 4 illustrates Akt-1 mRNA down-regulation in Panc-1 cells upon treatment of LCAN-RX-0201.

In vitro gene targeting efficiency of LCAN formulation containing RX-0201 (LCAN-RX-0201) was evaluated in KB and Panc-1 cells. In KB cells, LCAN-RX-0201 significantly decreased Akt-1 mRNA expression compared to LCAN-control at 1 μM of RX-0201 concentration (FIG. 3). In the same manner, Panc-1 cells treated by LCAN-RX-0201 showed the significant decrease of Akt-1 mRNA expression compared to LCAN-control or free RX-0201 at 1 μM of RX-0201 concentration (FIG. 4).

2. In Vivo Therapeutic Efficacy of L-RX-0047 and LCAN-RX-0047 in a KB Xenograft Tumor Model Therapeutic efficacies of free RX-0047, L-RX-0047, and LCAN-RX-0047 were evaluated in KB tumor xenograft carrying athymic nude mice. Female mice (18-22 g) were subcutaneously inoculated with $4 \times 10^6$ KB cells. When tumors reached a volume of 50-100 mm$^3$, the mice were randomly assigned to four groups (5 mice/group) and injected intravenously with 3 mg/kg of different formulation four times every three day (Q3Dx4). Tumor dimensions were determined by measurement with a caliper and tumor volumes (mm$^3$) were calculated by volume=0.5×(length×width×height). For analysis of the HIF-1α down-regulation, mice were scarified 24 hours after the last treatment. Tumors were then collected for analysis of HIF-1α gene expression. Animal survival was evaluated by Kaplan-Meier analysis.

Figure 5:
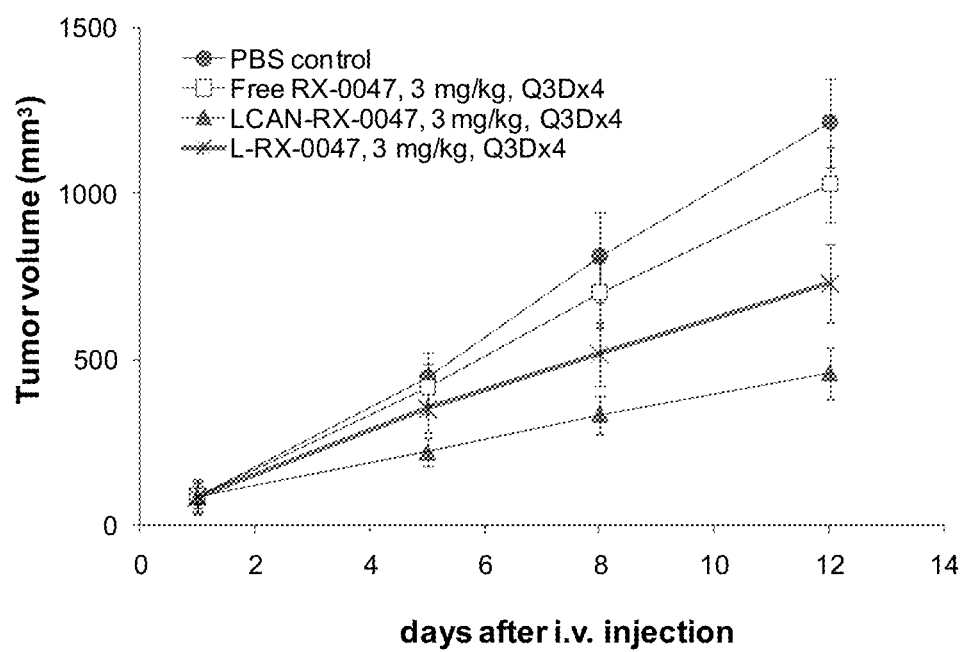
FIG. 5 illustrates in vivo tumor inhibition in KB xenograft tumor model. Mice (5 mice per group) were injected intravenously with 3 mg/kg of PBS, free RX-0047, L-RX-0047 or LCAN-RX-0047 four times every three day (Q3Dx4). Tumor dimensions were determined by measurement with a caliper every 3-4 days.

In vivo gene targeting efficiency of LCAN-RX-0047 was evaluated in KB xenograft tumor model. As shown in FIG. 5, free RX-0047 at dose of 3 mg/kg only slightly decreased tumor volume relative to the PBS control, although the difference was not significant. L-RX-0047 significantly decreased tumor growth compared to PBS control or free RX-0047 at dose of 3 mg/kg. In contrast, LCAN-RX-0047 was more significantly decreased tumor growth than L-RX-0047.

Figure 6:
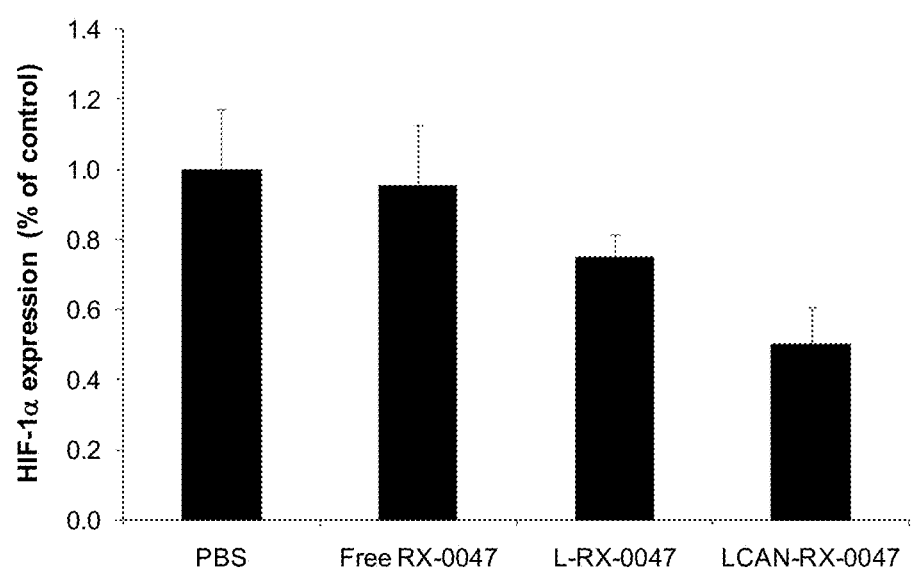
FIG. 6 illustrates in vivo HIF-1α mRNA expression in a KB xenograft tumor model. Mice (5 mice per group) were injected intravenously with 3 mg/kg of PBS, free RX-0047, L-RX-0047 or LCAN-RX-0047 four times every three day (Q3Dx4). Intratumoral expression of HIF-1α mRNA was determined by real-time RT-PCR.

Consistent with these data, the expression levels of HIF-1α in tumor tissues were significantly down-regulated by L-RX-0047 and LCAN-RX-0047 at dose of 3 mg/kg in KB xenograft mice (FIG. 6) and with LCAN formulation being much more active.

Figure 7:
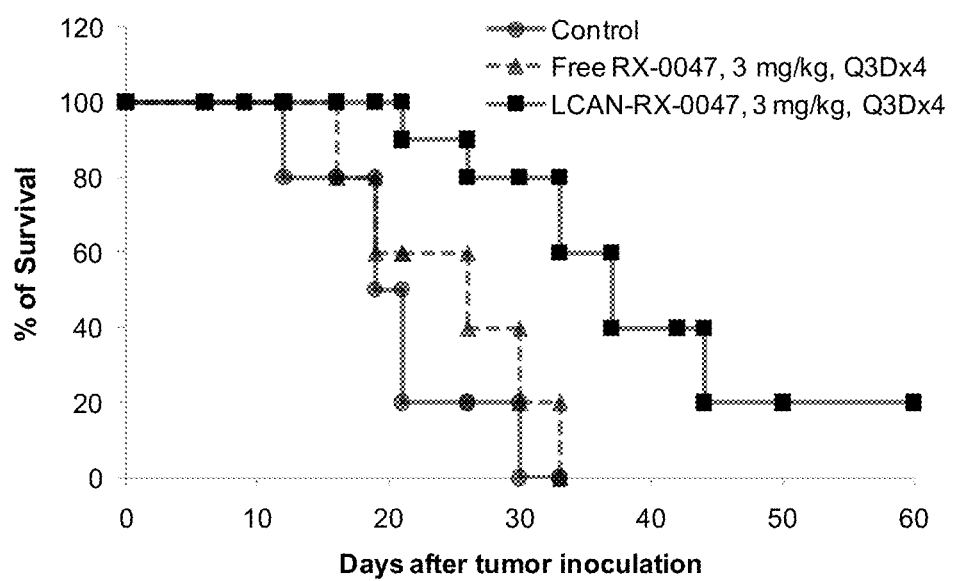
FIG. 7 illustrates animal survival upon treatment with of LCAN-RX-0047 in KB xenograft tumor model. Mice (10 mice per group) were injected intravenously with 3 mg/kg of PBS, free RX-0047 or LCAN-RX-0047 four times every three day (Q3Dx4).

Meanwhile, animal survival was evaluated by Kaplan-Meier analysis and increase-in-lifespan (ILS, %) was calculated by ILS=(mean survival time of the treated mice/mean survival time of control mice−1)×100%. Mice (10 mice per group) were injected intravenously with 3 mg/kg of PBS, free RX-0047 or LCAN-RX-0047 four times every three day (Q3Dx4). The median survival time (MeST) for PBS, free RX-0047, or LCAN-RX-0047 groups was 19, 26, and 37 days, respectively (FIG. 7). Percentage ILS values are 94.7% for LCAN-RX-0047. Moreover, 2 out of 10 mice were completely cured following treatment with LCAN-RX-0047. These results indicate that LCAN-RX-0047 has potent anticancer activity as a monotherapy.

Certain embodiments of the formulations and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A lipid nanoparticle composition comprising:
   a cationic liposome;
   a targeting agent; and
   a net positively-charged core comprising an albumin-polycation conjugate,
      wherein the cationic liposome encapsulates the net positively-charged core to form a lipid-coated albumin nanoparticle (LCAN).

2. The lipid nanoparticle composition of claim 1, the net positively-charged core further comprising a therapeutic agent selected from the group consisting of nucleic acids, proteins, polysaccharides, lipids, radioactive substances, prodrugs, and combinations thereof.

3. The lipid nanoparticle composition of claim 2, wherein the therapeutic agent comprises an antisense oligonucleotide (ASO) selected from the group consisting of
   an ASO targeted to a portion of a nucleic acid encoding Akt-1, and which modulates the expression of Akt-1; and
   an ASO targeted to a portion of a nucleic acid encoding HIF-1, and which modulates the expression of HIF-1.

4. The lipid nanoparticle composition of claim 1, wherein the albumin is human serum albumin (HSA).

5. The lipid nanoparticle composition of claim 1, wherein the albumin-polycation conjugate comprises pentaethylenehexamine (PEHA) or tetraethylenepentamine.

6. The lipid nanoparticle composition of claim 3, wherein the antisense oligonucleotide is a compound having a sequence comprising 5' gctgcatgatctccttggcg 3' (Seq. Id. No.: 1), targeted to a nucleic acid molecule encoding human Akt-1, and which modulates the expression of Akt-1.

7. The lipid nanoparticle composition of claim 3, wherein the antisense oligonucleotide is a compound having a sequence comprising 5'aatgagccaccagtgtccaa 3' (Seq. Id. No.: 2), targeted to a nucleic acid molecule encoding human HIF-1, and which modulates the expression of HIF-1.

8. The lipid nanoparticle composition of claim 1, wherein the targeting agent comprises a moiety selected from RGD peptides, galactose-containing moieties, transferrin, folate, low density lipoprotein, epidermal growth factors, and antibodies.

9. The lipid nanoparticle composition of claim 1, wherein the targeting agent comprises cRGDfC or folate.

10. The lipid nanoparticle composition of claim 1, wherein the targeting agent comprises a conjugate selected from the group consisting of folate-PEG-CHEMS (folate-polyethylene glycol-cholesteryl hemisuccinate), folate-PEG-DSPE (folate-polyethylene glycol-distearoyl phosphatidylethanolamine), and cRGDfC-PEG-DSPE (cyclo(RGDfC)-polyethylene glycol-distearoyl phosphatidylethanolamine).

11. A pharmaceutical composition comprising:
   a lipid nanoparticle composition comprising
      a cationic liposome;
      a targeting agent; and
      a net positively-charged core comprising an albumin-polycation conjugate and a therapeutic agent, wherein the cationic liposome encapsulates the net positively-charged core to form a lipid-coated albumin nanoparticle (LCAN); and
   a pharmaceutically acceptable excipient.

12. The pharmaceutical composition of claim 11, wherein the therapeutic agent is an antisense oligonucleotide (ASO) selected from the group consisting of an ASO targeted to a portion of a nucleic acid encoding Akt-1, and which modulates the expression of Akt-1; and an ASO targeted to a portion of a nucleic acid encoding HIF-1, and which modulates the expression of HIF-1.

13. A method of making a lipid-coated albumin nanoparticle (LCAN), the method comprising
   synthesizing a HSA-PEHA conjugate;
   preparing a mixture of lipids comprising a cationic lipid and a targeting agent;
   adding the mixture of lipids to the HSA-PEHA conjugate, wherein the mixture of lipids form a cationic liposome that encapsulates the HSA-PEHA conjugate; and
   adding a therapeutic agent to the mixture of lipids and the HSA-PEHA conjugate to obtain an LCAN precursor.

14. The method of claim 13, wherein the therapeutic agent comprises an antisense oligonucleotide (ASO) selected from the group consisting of an ASO targeted to a portion of a nucleic acid encoding Akt-1, and which modulates the expression of Akt-1; and an ASO targeted to a portion of a nucleic acid encoding HIF-1, and which modulates the expression of HIF-1.

15. The method of claim 13, further comprising adding the targeting agent to the cationic liposome and the HSA-PEHA conjugate.

16. The method of claim 15, wherein the lipids comprising a targeting agent selected from the group consisting of folate-PEG-CHEMS (folate-polyethylene glycol-cholesteryl hemisuccinate), folate-PEG-DSPE (folate-polyethylene glycol-distearoyl phosphatidylethanolamine), and cRGDfC-PEG-DSPE (cyclo(RGDfC)-polyethylene glycol-distearoyl phosphatidylethanolamine).

17. A method of treating a cancer or infectious disease, the method comprising administering an effective amount of a pharmaceutical composition of claim 11 to a patient in need thereof.

18. The method of claim 17, wherein the cancer is selected from the group consisting of brain cancer, bladder cancer, lung cancer, breast cancer, melanoma, skin cancer, epidermal carcinoma, colon and rectal cancer, non-Hodgkin lymphoma, endometrial cancer, pancreatic cancer, kidney cancer, prostate cancer, leukemia thyroid cancer, head and neck cancer, ovarian cancer, hepatocellular cancer, cervical cancer, sarcomas, gastric cancers, multiple myeloma, lymphomas, gastrointestinal cancer, and uterine cancer.

19. The lipid nanoparticle composition of claim 5, wherein the albumin-polycation conjugate is a HSA-PEHA conjugate.

20. The lipid nanoparticle composition of claim 1, wherein the albumin-polycation conjugate comprises polyethylenimine (PEI).

21. The lipid nanoparticle composition of claim 1, wherein the targeting agent is coated on the surface of the cationic liposome.

22. The lipid nanoparticle composition of claim 1, wherein the polycation comprises PEHA, wherein the mole ratio of the PEHA to the albumin is between 10 to 1 and 12 to 1.

23. The lipid nanoparticle composition of claim 22, wherein the mole ratio of the PEHA to the albumin is about 11 to 1.

24. The lipid nanoparticle composition of claim 1, wherein the cationic liposome comprises a cationic lipid selected from the group consisting of: 3β-[N(N',N'-dimethylaminoethane)-carbamoyl]cholesterol hydrochloride (DC-Chol); 1,2-dioleoyl-3-trimethylammonium-propane (DOTAP); 1,2-dioleoyl-3-dimethylammonium-propane (DODAP); dimethyldioctadecylammonium bromide salt (DDAB); 1,2-dilauroyl-sn-glycero-3-ethylphosphocholine chloride (DL-EPC); N-[1-(2,3-dioleyloyx) propyl]-N—N—N-trimethyl ammonium chloride (DOTMA); N-[1-(2,3-dioleyloyx) propyl]-N—N—N-dimethyl ammonium chloride (DODMA); 1,2-dilauroyl-sn-glycero-3-ethylphosphocholine chloride (DOEPC); N,N-dioctadecyl-N,N-dimethylammonium chloride (DODAC); N-(1-(2,3-dioleyloxy)propyl)-N-2-(sperminecarboxamido)ethyl)-N,N-dimethylammonium trifluoracetate (DOSPA); 1,2-dimyristyloxypropyl-3-dimethylhydroxyethyl ammonium bromide (DMRIE); dioctadecylamidoglycylspermine (DOGS); neutral lipids conjugated to cationic modifying groups; and combinations thereof.

25. The lipid nanoparticle composition of claim 1, further comprising a stabilizing component.

26. The lipid nanoparticle composition of claim 25, wherein the stabilizing component is selected from D-alpha tocopheryl polyethylene glycol 1000 succinate (TPGS) or mPEG-DSPE.

27. The method of claim 13, wherein the mixture of lipids comprises DOTAP, soyPC, and TPGS, and wherein the targeting agent comprises cRGDfC-PEG-DSPE.

28. The method of claim 27, wherein the molar ratio of DOTAP:soyPC:TPGS:cRGD-PEG-DSPE is about 25:70:4:1.

29. The lipid nanoparticle composition of claim 1, wherein the lipid nanoparticle has a particle size under about 300 nm.

30. The lipid nanoparticle composition of claim 1, wherein the lipid nanoparticle has a particle size under about 150 nm.

31. The lipid nanoparticle composition of claim 1, wherein the albumin-polycation conjugate comprises spermine or spermidine.

32. The lipid nanoparticle composition of claim 1, wherein the polycation is selected from the group consists of polyethylenimine (PEI); pentaethylenehexamine (PEHA); tetraethylenepentamine; spermine; spermidine; poly(L-lysine); poly(amido amine) (PAMAM) dendrimers; polypropyleneimine dendrimers; poly(2-dimethylamino ethyl)-methacrylate (pDMAEMA); chitosan; tris(2-aminoethyl) amine and its methylated derivatives; and combinations thereof.

* * * * *

UNITED STATES PATENT AND TRADEMARK OFFICE
CERTIFICATE OF CORRECTION

PATENT NO.         : 10,307,490 B2
APPLICATION NO.    : 13/900969
DATED              : June 4, 2019
INVENTOR(S)        : Robert J. Lee et al.

Page 1 of 1

It is certified that error appears in the above-identified patent and that said Letters Patent is hereby corrected as shown below:

In the Specification

Column 1, Line 16-19 replace the Government Support Clause with:
--This invention was made with government support under CA135243 awarded by the National Institutes of Health. The government has certain rights in the invention.--

Signed and Sealed this
Thirteenth Day of October, 2020

Andrei Iancu
*Director of the United States Patent and Trademark Office*